United States Patent [19]

Miyatake

[11] 4,210,808
[45] Jul. 1, 1980

[54] PNEUMATIC INFRARED ANALYZER OF THE SINGLE BEAM TYPE

[75] Inventor: Kimio Miyatake, Miyanohigashi, Japan

[73] Assignee: Horiba, Ltd., Kyoto, Japan

[21] Appl. No.: 941,638

[22] Filed: Sep. 12, 1978

[30] Foreign Application Priority Data

Oct. 26, 1977 [JP] Japan .................................. 52-128956

[51] Int. Cl.$^2$ .............................................. G01J 1/00
[52] U.S. Cl. ..................................... 250/343; 250/347
[58] Field of Search ....................... 250/343, 347, 353; 356/233, 437

[56] References Cited

U.S. PATENT DOCUMENTS

| 1,733,354 | 10/1929 | Mayer | 356/233 |
| 2,212,211 | 8/1940 | Pfund | 356/437 |
| 3,861,809 | 1/1975 | Hall, Jr. | 356/437 |
| 3,968,370 | 7/1976 | Luft | 250/343 |
| 4,020,345 | 4/1977 | Meyer | 250/343 |

Primary Examiner—Alfred E. Smith
Assistant Examiner—Janice A. Howell
Attorney, Agent, or Firm—Wenderoth, Lind & Ponack

[57] ABSTRACT

A detector for a single beam pneumatic infrared analyzer having two light receivers, a front receiver and a rear receiver positioned in series in the path of infrared light rays coming from a sample cell and each of which has a gas enclosed therein and used for measuring the concentration of a sample flowing through the sample cell by comparing the different absorption spectra of the infrared rays hitting the two receivers, and a screening device in front of the front light receiver for screening out the infrared rays in only the peripheral portions of the light, along the light path entering the front receiver.

4 Claims, 13 Drawing Figures

ADMITTANCE

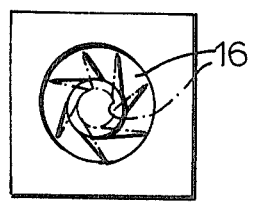
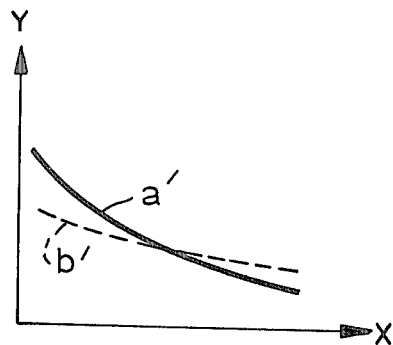
FIG.5　　　　　FIG.6
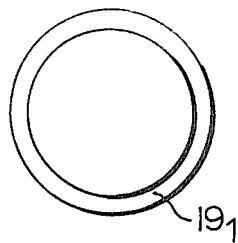 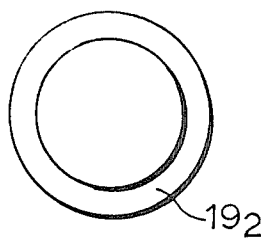 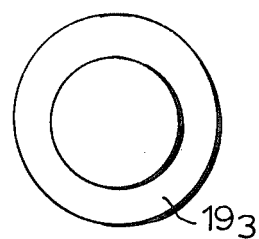
FIG.7a　FIG.7b　FIG.7c

PNEUMATIC INFRARED ANALYZER OF THE SINGLE BEAM TYPE

The present invention relates to a pneumatic infrared analyzer of the single beam type, provided with two light receivers, a front receiver and a rear receiver, which are positioned in series in the light path of infrared rays which are passed through a sample cell and each of which has a gas enclosed therearound for measuring the concentration of a sample flowing through the sample cell by the different absorption spectra of the infrared rays hitting the two receivers.

BACKGROUND OF THE INVENTION AND PRIOR ART

The construction of the detector portion of an infrared analyzer disclosed in Japanese Laid-Open Patent Application No. 90983/1977 is shown in FIG. 8 as an example of the prior art. In this device a front light receiver 20 and a rear light receiver 21 respectively enclose a control gas, which can be a gaseous component of a material contained in a sample to be analyzed or a known gas which absorbs an infrared spectra very similar to that absorbed by the gaseous sample to be analyzed, and the two receiver chambers 20 and 21 are connected to a condenser microphone detector 22 in order to sense the differences in the pressure changes in the two chambers 20 and 21 due to the absorption of the infrared rays as a charge in capacity. A screening plate 23 is provided between the front receiver 20 and the rear receiver 21 and is freely movable in and out of the space between the two receivers. By shifting the position of the screening plate 23 into and out of the path of the infrared rays and thus regulating the quantity of infrared rays absorbed in the rear receiver chamber 21, an optical balance between the infrared absorptions in the two receiver chambers can be achieved, as shown in FIG. 9, wherein the curve a shows the change in the signal due to the absorption of infrared rays in the front receiver chamber and the curve b shows the change in the rear receiver chamber, the quantity of infrared absorption being along the Y axis and the position of the screening plate being along the X axis.

However, in this prior art device, the construction of the detector is very complicated and there are several troublesome problems in the manufacture of the device, since the chambers 20 and 21 must be made independently. Furthermore, the stability of the screening plate 23 or the stabilizing of the plate at any given position is a difficult task.

In order to overcome the disadvantages of the prior art, there was experimentally developed a detector for an infrared analyzer as shown in FIG. 1, using an optical adjusting system like that used in an infrared analyzer of the double beam type in the analyzer of the single beam type. That is, the detector portion shown in FIG. 1 has a front receiver chamber 1 and a rear receiver chamber 2 which respectively enclose a reference gas, i.e. a gaseous component of a material contained in the sample gas to be analyzed or a known gas which absorbs an infrared spectra very similar to that absorbed by the gas to be analyzed. Both chambers 1 and 2 are connected to a condenser microphone detector 3, in order to detect the difference in pressure variations in the chambers 1 and 2 due to the absorption of infrared rays as a change in capacity (that is, a change of voltage in the detector 3).

In this infrared analyzer, as shown in FIGS. 1 and 2, a screening plate 4 was provided in front of the front receiver chamber 1 which was freely movable perpendicularly across the light path in order to adjust the quantities of light which enter the two receiver chambers 1 and 2. However, in this mechanism, since the screening plate 4 acts to control the amount of light admitted to the two receivers 1 and 2 in the same way, the signal curves a and b due to the absorption of infrared rays in the two chambers 1 and 2 were found to be almost parallel, as shown in FIG. 3, wherein the Y axis is the quantity of the absorbed infrared rays and the X axis is the position of the screening plate 4, and the curves a and b represent the change in the quantities of infrared rays absorbed respectively in the front receiver chamber 1 and the rear receiver chamber 2. Because of these characteristic curves, it was impossible to change the difference (b−a) effectively by movement of the screening plate 4 and accordingly, this analyzer could not be used to achieve an effective optical balance.

BRIEF SUMMARY OF THE INVENTION

In order to overcome the disadvantages of the experimentally developed analyzer while preserving its advantageous construction, the present invention provides a combination of a light screening means, a front light receiver, a rear light receiver and a condenser microphone detector in the same order as in the experimental analyzer, but the structure of the screening means has been changed so as to be completely different from the screening plate of the experimental analyzer. In the present invention, by providing a screening means which screens out the infrared rays by a gradually decreasing diameter aperture in front of the front receiver chamber, the rate of change of the signal from the front receiver is successfully increased so that it is much greater than that of the signal from the rear receiver. If only a zero point adjustment is desired, a ring shaped screening means which screens out the light beam and which is of a fixed type, i.e. not adjustable, will suffice.

BRIEF DESCRIPTION OF THE DRAWINGS

The invention will now be described in connection with the accompanying drawings, in which:

FIG. 5 is a diagramatic view showing the screening means of the present invention;

FIG. 6 is a graph showing the relation between signal changes in the receivers of the present invention due to the absorption of infrared rays;

FIGS. 7a–7c, 10 and 11 are examples of other screening means of the present invention;

DETAILED DESCRIPTION OF THE PREFERRED EMBODIMENT

Figure 1:
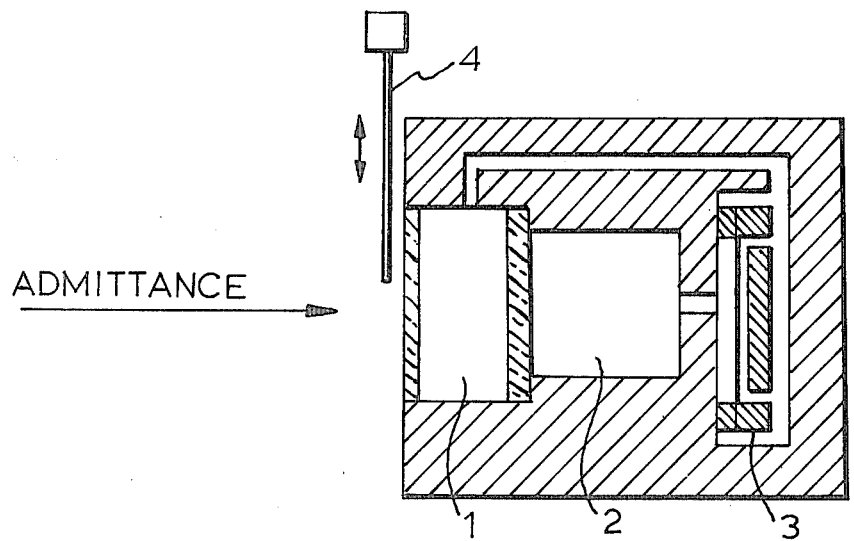
FIGS. 1 and 2 are a sectional view and a front elevation view showing an experimental analyzer developed by the present inventors.
Figure 2:
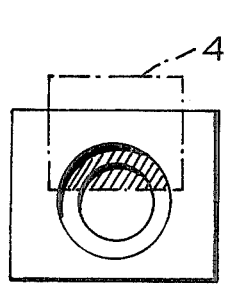
Figure 3:
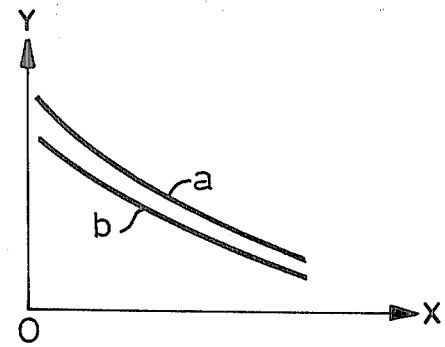
FIG. 3 is a graph showing the relation of signal changes in the light receivers.
Figure 4:
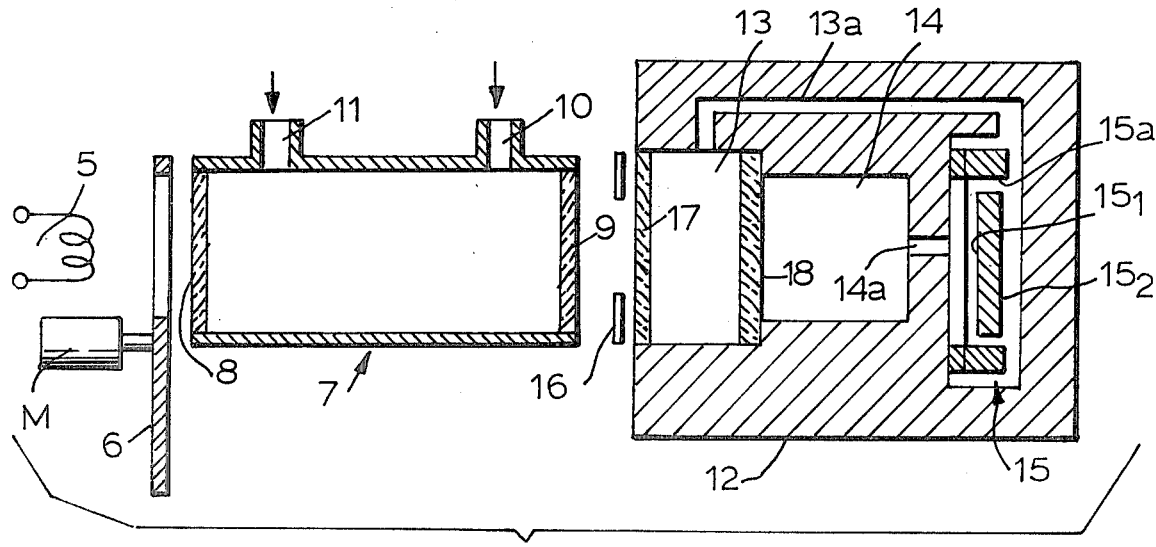
FIG. 4 is a longitudinal sectional view of an embodiment of the present invention.

As shown in detail in FIG. 4, a light source 5 emits a light flux of infrared rays. Spaced a certain distance from the light source 5 in the direction of the flow of the light is a chopper 6 which passes through the path of the infrared rays intermittently. The chopper 6 has a circular plate having holes therein and is driven in its rotation by a motor M. A sample cell 7 is positioned next along the path of the light rays and has windows 8 and 9 in the opposite ends for passing the light flux and a lateral inlet 10 and an outlet 11 for a sample gas. The infrared rays passed through the sample cell 7 are introduced into a detector 12, which has a front receiver chamber 13 and a rear receiver 14 which are arranged in series in the recited order in the path of the infrared rays. A condenser microphone detector 15 is provided in order to sense the differences in the pressure of a gas enclosed in each of the two receivers 13 and 14, as a voltage change. The diaphram $15_1$ of the condenser microphone detector 15 is located in a chamber 15a with one side exposed to the pressure in chamber 13 through passage 13a and the other side exposed to the pressure in chamber 14 through passage 14a. The electrode $15_2$ of the condenser microphone detector 15 is connection to an amplifier (not shown in the drawings). A screening means 16 is positioned just ahead of the front window 17 of the front receiver chamber 13 and in the present example, has a structure which is the same as that of an iris diaphragm mechanism used in a camera. Thus, the screening device is able to screen out the light beam by a gradually decreasing diameter aperture. It is possible by the use of an iris diaphragm mechanism to adjust the area of the aperture from that shown in full lines to that shown in dotted lines in FIG. 5.

A window 18 is provided between the front receiver 13 and the rear receiver 14. Thus, the light beam emitted from the light source 5 enters the detector 12 after passing through the sample cell 7 and the cross-sectional area of the light beam is regulated by the screening device 16, which screens out the outer portion of the beam as described above. There is thus produced from the detector 14 a signal a' which corresponds to the infrared absorption in the front receiver 13 and a signal b' which corresponds to the infrared absorption in the rear receiver 14. Experimentally observed curves a' and b' are as shown in FIG. 6, wherein the quantity of the absorbed infrared rays is shown on the Y axis and the degree of screening by the screening device on the X axis. It is easily understood from this figure that the tendency to change of the value of the signal due to a change of the degree of screening by the screening device 16 is much greater for the signal a' than for the signal b'.

This phenomenon is due to the fact that in the front receiver 13, a comparatively large amount of light enters from the outer portion of the beam near the periphery thereof, while in the rear receiver 14, only a small amount of light enters from the outer portion of the beam and almost all of the light is light from near the center of the beam since the rear receiver 14 is relatively far from the window 17. At any rate, in the present invention, by providing a screening device, as described above, just ahead of the front receiver chamber which screens out the portion of the light near the periphery of the beam, it becomes possible to adjust the degree of screening, when necessary, and thus changing to a large degree the amount of light which enters the front receiver. Thus, since the invention makes it possible to increase the change of the signal due to the infrared absorption in the front receiver to a larger degree than for the signal due to the absorption in the rear receiver, the zero point adjustment or span check is made possible by an effective change of difference between the two signals generated by the absorptions in the two receiver chambers. Thus, the invention succeeds in providing an easy and effective optical adjustment which has up to now not been found in the prior art.

Figure 8:
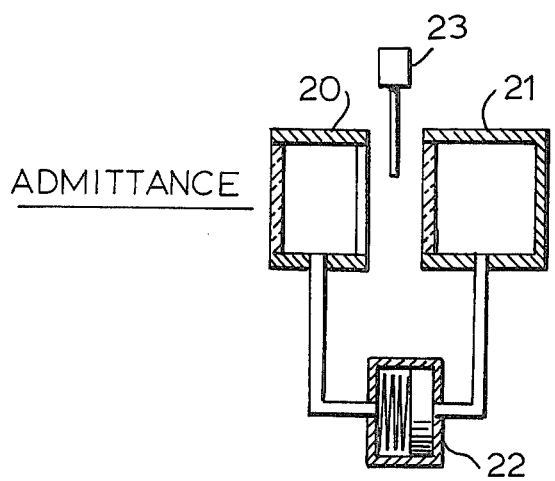
FIG. 8 shows a detector portion of a prior art analyzer.
Figure 9:
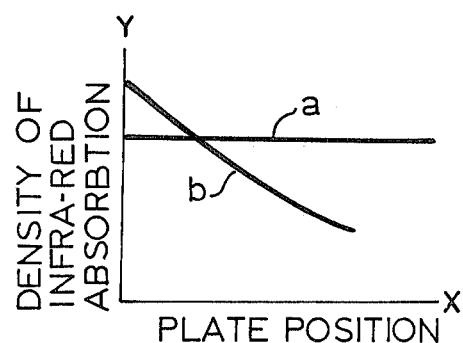
FIG. 9 is a graph showing the relation between the position of the screening plate of the apparatus shown in FIG. 8 and the quantity of the absorbed infrared rays.

Furthermore, it is noted that in the prior art device such as shown in FIG. 8, wherein a conventional screening plate is used in the detector, the infrared analyzer can never be compact since it is necessary to provide sufficient space in the detector to slide the screening plate freely into or out of the light beam. However, in the present invention, the infrared analyzer can be manufactured in a compact style since it is not necessary to have extra space for a sliding screener.

Figure 10:
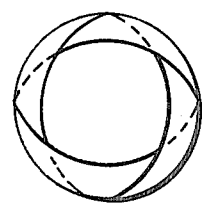
Figure 11:
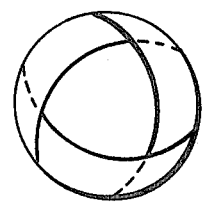

The screening device of the present invention is not limited to the specific iris type diaphragm shown in FIG. 5. Besides the iris diaphragm generally used in a camera, other similar aperture forming devices which make it possible to perform an effective optical adjustment can be used. The screening can be effectively carried out in accordance with the present invention using screening devices such as ring screeners as shown in FIGS. 10 and 11. Fixed aperture size screeners having an annular shape, such as rings $19_1$, $19_2$ and $19_3$ in FIGS. 7a-7c, etc., can be used by fixing them tightly just ahead of the front receiver. These rings can be interchangable. Moreover, the optical adjustment technique of the present invention can also be used in an infrared analyzer of the pneumatic type using a detector of another type, such as a micro-flowsensor.

From the foregoing, it will be seen that the present invention provides a screening device, such as for example, an iris diaphragm, just ahead of a front receiver of light, which screens out the outer peripheral part of the light going into the front receiver while not substantially affecting the amount of light going into the rear receiver which is attached to the front receiver. The arrangement according to the invention has thus made is possible to overcome the disadvantages of separate front and rear receivers and to manufacture a single beam infrared analyzer with the front and rear receivers joined to each other.

What is claimed is:

1. A detector means for a single beam pneumatic infrared analyzer, comprising:

a front light receiver means contained within a first containing structure, said containing structure further containing therein a control gas;

a rear light receiver means positioned in series behind said front light receiver means, said rear light receiver means being contained within a second containing structure, said second containing structure further containing said same control gas as said first containing structure;

sample cell means positioned in front of said front receiver means, said sample cell means containing a sample gas;

infrared light source means for directing infrared light through said sample cell means and said sample gas, said infrared light further striking said receiver means for determining the concentration of said sample in said sample cell means according to the difference in absorption of said infrared rays at said two receiver means; and adjustable light admission means positioned between said sample cell means and said two receiver means for blocking out the peripheral portions of said infrared light entering said front receiver means.

2. A detector means as claimed in claim 1 in which said adjustable light admission means is an iris diaphragm.

3. A detector as claimed in claim 1 in which said screening device is an annular ring mounted in front of said front receiver means.

4. A detector as claimed in claim 1 in which said front and rear receiver means is a micro-flowsensor.

* * * * *